United States Patent
Hughes et al.

(10) Patent No.: US 7,217,415 B1
(45) Date of Patent: May 15, 2007

(54) NADP-DEPENDENT GLYCERALDEHYDE-3-PHOSPHATE DEHYDROGENASE FOR THERAPEUTIC USE

(75) Inventors: Martin John Glenton Hughes, Berkshire (GB); Joseph David Santangelo, Berkshire (GB); Jonathan Douglas Lane, Berkshire (GB); Robert Feldman, Berkshire (GB); Joanne Christine Moore, Berkshire (GB); Richard James Dobson, Berkshire (GB); Paul Everest, Dumbartonshire (GB); Caroline Joanne Henwood, Hertfordshire (GB); Gordon Dougan, London (GB); Rebecca Kerry Wilson, London (GB)

(73) Assignee: Emergent Product Development UK Limited (GB)

( * ) Notice: Subject to any disclaimer, the term of this patent is extended or adjusted under 35 U.S.C. 154(b) by 0 days.

(21) Appl. No.: 09/868,195

(22) PCT Filed: Dec. 22, 1999

(86) PCT No.: PCT/GB99/04376

§ 371 (c)(1),
(2), (4) Date: Sep. 14, 2001

(87) PCT Pub. No.: WO00/37490

PCT Pub. Date: Jun. 29, 2000

(30) Foreign Application Priority Data

| Dec. 22, 1998 | (GB) | 9828346.8 |
| Jan. 20, 1999 | (GB) | 9901233.8 |
| Jan. 20, 1999 | (GB) | 9901234.6 |
| Apr. 12, 1999 | (GB) | 9908321.4 |
| May 24, 1999 | (GB) | 9912036.2 |
| Sep. 23, 1999 | (GB) | 9922596.3 |

(51) Int. Cl.
*A61K 38/54* (2006.01)
*C12N 9/06* (2006.01)

(52) U.S. Cl. .............. 424/94.4; 424/190.1; 435/191

(58) Field of Classification Search ............ 424/184.1, 424/185.1, 190.1, 234.1, 244.1, 93.1, 93.44
See application file for complete search history.

(56) References Cited

U.S. PATENT DOCUMENTS 6,248,329 B1 * 6/2001 Chandrashekar et al. 424/191.1

FOREIGN PATENT DOCUMENTS

| EP | 0230777 | 8/1987 |
| EP | 0913476 | 5/1999 |
| WO | 9410317 | 5/1994 |
| WO | 9421685 | 9/1994 |
| WO | 9823631 | 6/1998 |

OTHER PUBLICATIONS

Itoh et al, (Microbiology and Immunology, 30(4):297-306, 1986).*
Ichiman et al (Canadian Journal of Microbiology 28(7):726-732, 1982).*
Houghten et al. (New Approaches to Immunization, Vaccines86, Cold Spring Harbor Laboratory, p. 21-25, 1986).*
McGuinnes et al. (Lancet 337: 514-517, Mar. 1991).*
McGuinnes et al. (Mol. Microbiol. 7: 505-514, Feb. 1993).*
Feng et al (Infection and Immunity, 64(1):363-365, 1996).*
Ellis, R.W. (Chapter 29 of "VACCINES" [Plotkin, S.A. et al. (eds) published by W. B. Saunders company (Philadephia) in 1988.*
Brown et al (Biochem. Biophys. Res. Commun. 43(1):217-24.*
Kolberg et al (Infection and Immunity 64(9):3544-3547, 1996.*
Herbert et al, in The Dictionary of Immunology 4th edition, p. 2, 88, 90, 125 Academic Press, 1995.*
Hassett et al, Journal of Virology, 71(10):7881-7888, 1997.*
Stedman's Medical Dictionary on line.*
Larsson, Charlotte, Margaretha Stalhammar-Carlemalm, and Gunnar Lindahl (Sep. 1996) "Experimental Vaccination against Group B *Streptococcus*, and Encapsulated Bacteriu, with Highly Purified Preparations of Cell Surface Proteins Rib and α" *Infection and Immunity* 64(9):3518-3523.
Tricot, Catherine, Jean-Louis De Coen, Patricia Momin, Paul Falmagne and Victor Stalon (1989) "Evolutionary Relationships among Bacterial Carbamoyltransferases" *Journal of General Microbiology* 135:2453-2464.

* cited by examiner

*Primary Examiner*—Patricia A. Duffy
(74) *Attorney, Agent, or Firm*—Saliwanchik, Lloyd & Saliwanchik

(57) ABSTRACT

According to the present invention, a series of genes are identified in Group B *Streptococcus*, the products of which may be located on the outer surface of the organism. The genes, or functional fragments thereof, may be useful in the preparation of therapeutics, e.g. vaccines for the immunization of a patient against microbial infection.

6 Claims, No Drawings

SEQUENCE LISTING

<160> NUMBER OF SEQ ID NOS: 12

<210> SEQ ID NO 1
<211> LENGTH: 1014

```
<212> TYPE: DNA
<213> ORGANISM: Streptococcus agalactiae
<220> FEATURE:
<221> NAME/KEY: CDS
<222> LOCATION: (1)..(1014)
<223> OTHER INFORMATION:

<400> SEQUENCE: 1
```

| | | | | | | | | | | | | | | | | |
|---|---|---|---|---|---|---|---|---|---|---|---|---|---|---|---|---|
| atg | aca | caa | gta | ttt | caa | gga | cgt | agt | ttc | tta | gca | gaa | aaa | gat | ttt | 48 |
| Met | Thr | Gln | Val | Phe | Gln | Gly | Arg | Ser | Phe | Leu | Ala | Glu | Lys | Asp | Phe | |
| 1 | | | | 5 | | | | | 10 | | | | | 15 | | |
| tct | cgt | gag | gaa | ttt | gaa | tat | ctt | att | gat | ttt | tca | gct | cat | tta | aaa | 96 |
| Ser | Arg | Glu | Glu | Phe | Glu | Tyr | Leu | Ile | Asp | Phe | Ser | Ala | His | Leu | Lys | |
| | | | 20 | | | | | 25 | | | | | 30 | | | |
| gac | ctt | aaa | aaa | cgt | ggt | gtt | cct | cat | cat | tat | ctt | gaa | ggt | aaa | aat | 144 |
| Asp | Leu | Lys | Lys | Arg | Gly | Val | Pro | His | His | Tyr | Leu | Glu | Gly | Lys | Asn | |
| | | 35 | | | | | 40 | | | | | 45 | | | | |
| att | gct | ctc | tta | ttt | gaa | aaa | aca | tct | act | cgt | act | cgc | gca | gcc | ttt | 192 |
| Ile | Ala | Leu | Leu | Phe | Glu | Lys | Thr | Ser | Thr | Arg | Thr | Arg | Ala | Ala | Phe | |
| | 50 | | | | | 55 | | | | | 60 | | | | | |
| aca | act | gca | gca | att | gac | cta | ggc | gct | cat | ccg | gaa | tac | ctt | ggt | gca | 240 |
| Thr | Thr | Ala | Ala | Ile | Asp | Leu | Gly | Ala | His | Pro | Glu | Tyr | Leu | Gly | Ala | |
| 65 | | | | | 70 | | | | | 75 | | | | | 80 | |
| aat | gat | att | caa | ctt | ggt | aaa | aaa | gaa | tca | aca | gaa | gat | act | gct | aag | 288 |
| Asn | Asp | Ile | Gln | Leu | Gly | Lys | Lys | Glu | Ser | Thr | Glu | Asp | Thr | Ala | Lys | |
| | | | | 85 | | | | | 90 | | | | | 95 | | |
| gtt | tta | gga | cgt | atg | ttt | gat | ggt | att | gaa | ttc | cgt | ggt | ttt | agc | caa | 336 |
| Val | Leu | Gly | Arg | Met | Phe | Asp | Gly | Ile | Glu | Phe | Arg | Gly | Phe | Ser | Gln | |
| | | | 100 | | | | | 105 | | | | | 110 | | | |
| aga | atg | gtt | gaa | gag | ctt | gct | gaa | ttt | tct | gga | gta | cct | gtc | tgg | aat | 384 |
| Arg | Met | Val | Glu | Glu | Leu | Ala | Glu | Phe | Ser | Gly | Val | Pro | Val | Trp | Asn | |
| | | 115 | | | | | 120 | | | | | 125 | | | | |
| ggt | tta | aca | gat | gaa | tgg | cat | cca | aca | caa | atg | cta | gct | gac | tac | ctt | 432 |
| Gly | Leu | Thr | Asp | Glu | Trp | His | Pro | Thr | Gln | Met | Leu | Ala | Asp | Tyr | Leu | |
| | 130 | | | | | 135 | | | | | 140 | | | | | |
| act | atc | aaa | gaa | aac | ttc | ggt | aaa | ctt | gaa | ggt | att | act | ctt | gtt | tac | 480 |
| Thr | Ile | Lys | Glu | Asn | Phe | Gly | Lys | Leu | Glu | Gly | Ile | Thr | Leu | Val | Tyr | |
| 145 | | | | | 150 | | | | | 155 | | | | | 160 | |
| tgt | ggt | gac | gga | cgt | aac | aat | gtt | gcc | aac | tcg | ctt | tta | gtg | gct | ggg | 528 |
| Cys | Gly | Asp | Gly | Arg | Asn | Asn | Val | Ala | Asn | Ser | Leu | Leu | Val | Ala | Gly | |
| | | | | 165 | | | | | 170 | | | | | 175 | | |
| act | ttg | atg | ggg | gtc | aat | gta | cac | atc | ttt | tct | cca | aaa | gaa | ctt | tty | 576 |
| Thr | Leu | Met | Gly | Val | Asn | Val | His | Ile | Phe | Ser | Pro | Lys | Glu | Leu | Phe | |
| | | | 180 | | | | | 185 | | | | | 190 | | | |
| ccw | gct | gaa | gag | att | gtt | aaa | ttg | gct | gaa | gga | tat | gcc | aaa | gaa | tct | 624 |
| Pro | Ala | Glu | Glu | Ile | Val | Lys | Leu | Ala | Glu | Gly | Tyr | Ala | Lys | Glu | Ser | |
| | | 195 | | | | | 200 | | | | | 205 | | | | |
| ggg | gct | cac | gtt | ctc | gtt | act | gat | aat | gta | gac | gaa | gct | gta | aag | gga | 672 |
| Gly | Ala | His | Val | Leu | Val | Thr | Asp | Asn | Val | Asp | Glu | Ala | Val | Lys | Gly | |
| | 210 | | | | | 215 | | | | | 220 | | | | | |
| gca | gac | gtc | ttt | tac | act | gat | gtc | tgg | gta | tcg | atg | gga | gaa | gaa | gat | 720 |
| Ala | Asp | Val | Phe | Tyr | Thr | Asp | Val | Trp | Val | Ser | Met | Gly | Glu | Glu | Asp | |
| 225 | | | | | 230 | | | | | 235 | | | | | 240 | |
| aag | ttc | aaa | gaa | cgc | gtt | gaa | ctt | ctt | caa | cca | tat | caa | gta | aac | atg | 768 |
| Lys | Phe | Lys | Glu | Arg | Val | Glu | Leu | Leu | Gln | Pro | Tyr | Gln | Val | Asn | Met | |
| | | | | 245 | | | | | 250 | | | | | 255 | | |
| gaa | ctg | att | aaa | aaa | gct | aat | aat | gat | aat | ctt | atc | ttc | tta | cac | tgc | 816 |
| Glu | Leu | Ile | Lys | Lys | Ala | Asn | Asn | Asp | Asn | Leu | Ile | Phe | Leu | His | Cys | |
| | | | 260 | | | | | 265 | | | | | 270 | | | |
| tta | cct | gca | ttc | cat | gat | aca | aat | acc | gtt | tat | ggc | aaa | gac | gtc | gct | 864 |
| Leu | Pro | Ala | Phe | His | Asp | Thr | Asn | Thr | Val | Tyr | Gly | Lys | Asp | Val | Ala | |

```
                    275                 280                 285
gaa aaa ttt ggg gtc aag gaa atg gaa gtt act gat gaa gtc ttc cgt        912
Glu Lys Phe Gly Val Lys Glu Met Glu Val Thr Asp Glu Val Phe Arg
    290                 295                 300 agc aaa tat gct cgt cat ttc gac caa gct gaa aat cgt atg cac act        960
Ser Lys Tyr Ala Arg His Phe Asp Gln Ala Glu Asn Arg Met His Thr
305                 310                 315                 320 att aaa gct gta atg gct gca acc ctt gga aat ctt ttc att cca aaa       1008
Ile Lys Ala Val Met Ala Ala Thr Leu Gly Asn Leu Phe Ile Pro Lys
                325                 330                 335 gtt taa                                                                1014
Val
```

<210> SEQ ID NO 2
<211> LENGTH: 337
<212> TYPE: PRT
<213> ORGANISM: Streptococcus agalactiae

<400> SEQUENCE: 2

```
Met Thr Gln Val Phe Gln Gly Arg Ser Phe Leu Ala Glu Lys Asp Phe
1               5                   10                  15

Ser Arg Glu Glu Phe Glu Tyr Leu Ile Asp Phe Ser Ala His Leu Lys
            20                  25                  30

Asp Leu Lys Lys Arg Gly Val Pro His His Tyr Leu Glu Gly Lys Asn
        35                  40                  45

Ile Ala Leu Leu Phe Glu Lys Thr Ser Thr Arg Thr Arg Ala Ala Phe
    50                  55                  60

Thr Thr Ala Ala Ile Asp Leu Gly Ala His Pro Glu Tyr Leu Gly Ala
65                  70                  75                  80

Asn Asp Ile Gln Leu Gly Lys Lys Glu Ser Thr Glu Asp Thr Ala Lys
                85                  90                  95

Val Leu Gly Arg Met Phe Asp Gly Ile Glu Phe Arg Gly Phe Ser Gln
            100                 105                 110

Arg Met Val Glu Glu Leu Ala Glu Phe Ser Gly Val Pro Val Trp Asn
        115                 120                 125

Gly Leu Thr Asp Glu Trp His Pro Thr Gln Met Leu Ala Asp Tyr Leu
    130                 135                 140

Thr Ile Lys Glu Asn Phe Gly Lys Leu Glu Gly Ile Thr Leu Val Tyr
145                 150                 155                 160

Cys Gly Asp Gly Arg Asn Asn Val Ala Asn Ser Leu Leu Val Ala Gly
                165                 170                 175

Thr Leu Met Gly Val Asn Val His Ile Phe Ser Pro Lys Glu Leu Phe
            180                 185                 190

Pro Ala Glu Glu Ile Val Lys Leu Ala Glu Gly Tyr Ala Lys Glu Ser
        195                 200                 205

Gly Ala His Val Leu Val Thr Asp Asn Val Asp Glu Ala Val Lys Gly
    210                 215                 220

Ala Asp Val Phe Tyr Thr Asp Val Trp Val Ser Met Gly Glu Glu Asp
225                 230                 235                 240

Lys Phe Lys Glu Arg Val Glu Leu Leu Gln Pro Tyr Gln Val Asn Met
                245                 250                 255

Glu Leu Ile Lys Lys Ala Asn Asn Asp Asn Leu Ile Phe Leu His Cys
            260                 265                 270

Leu Pro Ala Phe His Asp Thr Asn Thr Val Tyr Gly Lys Asp Val Ala
        275                 280                 285
```

```
                Glu Lys Phe Gly Val Lys Glu Met Glu Val Thr Asp Glu Val Phe Arg
                    290                 295                 300

Ser Lys Tyr Ala Arg His Phe Asp Gln Ala Glu Asn Arg Met His Thr
                305                 310                 315                 320

Ile Lys Ala Val Met Ala Ala Thr Leu Gly Asn Leu Phe Ile Pro Lys
                                325                 330                 335

Val

<210> SEQ ID NO 3
<211> LENGTH: 1197
<212> TYPE: DNA
<213> ORGANISM: Streptococcus agalactiae
<220> FEATURE:
<221> NAME/KEY: CDS
<222> LOCATION: (1)..(1197)
<223> OTHER INFORMATION:

<400> SEQUENCE: 3 atg gct aaa ttg act gtt aaa gac gtt gat ttg aag gta aaa aaa gtc      48
Met Ala Lys Leu Thr Val Lys Asp Val Asp Leu Lys Val Lys Lys Val
1               5                   10                  15 ctc gtt cgt gtt gac ttt aat gtg cct ttg aaa gac ggc gtt atc act      96
Leu Val Arg Val Asp Phe Asn Val Pro Leu Lys Asp Gly Val Ile Thr
                20                  25                  30 aac gac aac cgt atc act gcg gct ctt cca aca atc aag tat atc atc     144
Asn Asp Asn Arg Ile Thr Ala Ala Leu Pro Thr Ile Lys Tyr Ile Ile
            35                  40                  45 gaa caa ggt ggt cgt gct atc ctc ttc tct cac ctt gga cgt gtt aaa     192
Glu Gln Gly Gly Arg Ala Ile Leu Phe Ser His Leu Gly Arg Val Lys
        50                  55                  60 gaa gaa gct gac aaa gaa gga aaa tca ctt gca ccg gta gct gct gat     240
Glu Glu Ala Asp Lys Glu Gly Lys Ser Leu Ala Pro Val Ala Ala Asp
65                  70                  75                  80 tta gct gct aaa ctt ggt caa gat gtt gta ttc cca ggt gtt act cgt     288
Leu Ala Ala Lys Leu Gly Gln Asp Val Val Phe Pro Gly Val Thr Arg
                85                  90                  95 ggt gca aaa tta gaa gaa gca atc aat gct ttg gaa gat gga caa gtt     336
Gly Ala Lys Leu Glu Glu Ala Ile Asn Ala Leu Glu Asp Gly Gln Val
            100                 105                 110 ctt ttg gtt gaa aac act cgt ttt gaa gat gtt gac ggt aag aaa gaa     384
Leu Leu Val Glu Asn Thr Arg Phe Glu Asp Val Asp Gly Lys Lys Glu
        115                 120                 125 tct aag aat gac gaa gaa ctt ggt aaa tac tgg gct tca ctt gga gat     432
Ser Lys Asn Asp Glu Glu Leu Gly Lys Tyr Trp Ala Ser Leu Gly Asp
130                 135                 140 gga atc ttc gtt aac gat gca ttt ggt aca gca cac cgt gct cat gca     480
Gly Ile Phe Val Asn Asp Ala Phe Gly Thr Ala His Arg Ala His Ala
145                 150                 155                 160 tca aac gta ggt att tca gca aac gtt gaa aaa gct gta gct ggt ttc     528
Ser Asn Val Gly Ile Ser Ala Asn Val Glu Lys Ala Val Ala Gly Phe
                165                 170                 175 ctt ctt gaa aac gaa att gct tac atc caa gaa gca gtt gaa act cca     576
Leu Leu Glu Asn Glu Ile Ala Tyr Ile Gln Glu Ala Val Glu Thr Pro
            180                 185                 190 gaa cgc cca ttc gta gct att ctt ggt ggc tca aaa gtt tct gat aag     624
Glu Arg Pro Phe Val Ala Ile Leu Gly Gly Ser Lys Val Ser Asp Lys
        195                 200                 205 att ggt gtt atc gaa aac ctt ctt gaa aaa gct gat aaa gtt ctt atc     672
Ile Gly Val Ile Glu Asn Leu Leu Glu Lys Ala Asp Lys Val Leu Ile
210                 215                 220
```

```
                                                                     -continued ggt ggt ggt atg act tac aca ttc tac aaa gct caa ggt atc gaa atc       720
Gly Gly Gly Met Thr Tyr Thr Phe Tyr Lys Ala Gln Gly Ile Glu Ile
225                 230                 235                 240 ggt aac tca ctt gta gaa gaa gac aaa ttg gat gtt gct aaa gac ctc       768
Gly Asn Ser Leu Val Glu Glu Asp Lys Leu Asp Val Ala Lys Asp Leu
            245                 250                 255 ctt gaa aaa tca aac ggt aaa ttg atc ttg cca gtt gac tca aaa gaa       816
Leu Glu Lys Ser Asn Gly Lys Leu Ile Leu Pro Val Asp Ser Lys Glu
        260                 265                 270 gca aac gca ttt gct ggt tat act gaa gtt cgc gac act gaa ggt gaa       864
Ala Asn Ala Phe Ala Gly Tyr Thr Glu Val Arg Asp Thr Glu Gly Glu
    275                 280                 285 gca gtt tca gaa ggg ttc ctt ggt ctt gac atc ggt cct aaa tca atc       912
Ala Val Ser Glu Gly Phe Leu Gly Leu Asp Ile Gly Pro Lys Ser Ile
290                 295                 300 gct aaa ttt gat gaa gca ctt act ggt gct aaa aca gtt gta tgg aac       960
Ala Lys Phe Asp Glu Ala Leu Thr Gly Ala Lys Thr Val Val Trp Asn
305                 310                 315                 320 gga cct atg ggt gtc ttt gaa aac cct gac ttc caa gct ggt aca atc      1008
Gly Pro Met Gly Val Phe Glu Asn Pro Asp Phe Gln Ala Gly Thr Ile
            325                 330                 335 ggt gta atg gac gct atc gtt aaa caa cca ggc gtt aaa tca atc atc      1056
Gly Val Met Asp Ala Ile Val Lys Gln Pro Gly Val Lys Ser Ile Ile
        340                 345                 350 ggt ggt ggt gat tca gca gca gct gct atc aac ctt ggt cgt gct gac      1104
Gly Gly Gly Asp Ser Ala Ala Ala Ala Ile Asn Leu Gly Arg Ala Asp
    355                 360                 365 aaa ttc tca tgg atc tct act ggt ggt gga gca agc atg gaa ttg ctc      1152
Lys Phe Ser Trp Ile Ser Thr Gly Gly Gly Ala Ser Met Glu Leu Leu
370                 375                 380 gaa ggt aaa gta tta cca ggt ttg gca gca ttg act gaa aaa taa          1197
Glu Gly Lys Val Leu Pro Gly Leu Ala Ala Leu Thr Glu Lys
385                 390                 395

<210> SEQ ID NO 4
<211> LENGTH: 398
<212> TYPE: PRT
<213> ORGANISM: Streptococcus agalactiae

<400> SEQUENCE: 4

Met Ala Lys Leu Thr Val Lys Asp Val Asp Leu Lys Val Lys Lys Val
1               5                   10                  15

Leu Val Arg Val Asp Phe Asn Val Pro Leu Lys Asp Gly Val Ile Thr
            20                  25                  30

Asn Asp Asn Arg Ile Thr Ala Ala Leu Pro Thr Ile Lys Tyr Ile Ile
        35                  40                  45

Glu Gln Gly Gly Arg Ala Ile Leu Phe Ser His Leu Gly Arg Val Lys
    50                  55                  60

Glu Glu Ala Asp Lys Glu Gly Lys Ser Leu Ala Pro Val Ala Ala Asp
65                  70                  75                  80

Leu Ala Ala Lys Leu Gly Gln Asp Val Val Phe Pro Gly Val Thr Arg
                85                  90                  95

Gly Ala Lys Leu Glu Glu Ala Ile Asn Ala Leu Glu Asp Gly Gln Val
            100                 105                 110

Leu Leu Val Glu Asn Thr Arg Phe Glu Asp Val Asp Gly Lys Lys Glu
        115                 120                 125

Ser Lys Asn Asp Glu Glu Leu Gly Lys Tyr Trp Ala Ser Leu Gly Asp
    130                 135                 140
```

-continued

```
Gly Ile Phe Val Asn Asp Ala Phe Gly Thr Ala His Arg Ala His Ala
145                 150                 155                 160

Ser Asn Val Gly Ile Ser Ala Asn Val Glu Lys Ala Val Ala Gly Phe
                165                 170                 175

Leu Leu Glu Asn Glu Ile Ala Tyr Ile Gln Glu Ala Val Glu Thr Pro
            180                 185                 190

Glu Arg Pro Phe Val Ala Ile Leu Gly Gly Ser Lys Val Ser Asp Lys
        195                 200                 205

Ile Gly Val Ile Glu Asn Leu Leu Glu Lys Ala Asp Lys Val Leu Ile
    210                 215                 220

Gly Gly Gly Met Thr Tyr Thr Phe Tyr Lys Ala Gln Gly Ile Glu Ile
225                 230                 235                 240

Gly Asn Ser Leu Val Glu Asp Lys Leu Asp Val Ala Lys Asp Leu
                245                 250                 255

Leu Glu Lys Ser Asn Gly Lys Leu Ile Leu Pro Val Asp Ser Lys Glu
            260                 265                 270

Ala Asn Ala Phe Ala Gly Tyr Thr Glu Val Arg Asp Thr Glu Gly Glu
        275                 280                 285

Ala Val Ser Glu Gly Phe Leu Gly Leu Asp Ile Gly Pro Lys Ser Ile
    290                 295                 300

Ala Lys Phe Asp Glu Ala Leu Thr Gly Ala Lys Thr Val Val Trp Asn
305                 310                 315                 320

Gly Pro Met Gly Val Phe Glu Asn Pro Asp Phe Gln Ala Gly Thr Ile
                325                 330                 335

Gly Val Met Asp Ala Ile Val Lys Gln Pro Gly Val Lys Ser Ile Ile
            340                 345                 350

Gly Gly Gly Asp Ser Ala Ala Ala Ile Asn Leu Gly Arg Ala Asp
        355                 360                 365

Lys Phe Ser Trp Ile Ser Thr Gly Gly Ala Ser Met Glu Leu Leu
    370                 375                 380

Glu Gly Lys Val Leu Pro Gly Leu Ala Ala Leu Thr Glu Lys
385                 390                 395
```

<210> SEQ ID NO 5
<211> LENGTH: 516
<212> TYPE: DNA
<213> ORGANISM: Streptococcus agalactiae
<220> FEATURE:
<221> NAME/KEY: CDS
<222> LOCATION: (1)..(516)
<223> OTHER INFORMATION:

<400> SEQUENCE: 5

```
atg aca cat att aca ttt gac tta ttc aaa gtc ttg ggt caa ttt gta      48
Met Thr His Ile Thr Phe Asp Leu Phe Lys Val Leu Gly Gln Phe Val
1               5                   10                  15 ggc gaa cac gag tta gac tac cta cca cca caa gta agt gca gca gat     96
Gly Glu His Glu Leu Asp Tyr Leu Pro Pro Gln Val Ser Ala Ala Asp
            20                  25                  30 gct ttc ctt cgt caa ggg act ggt cct gga tca gat ttt ctc gga tgg    144
Ala Phe Leu Arg Gln Gly Thr Gly Pro Gly Ser Asp Phe Leu Gly Trp
        35                  40                  45 atg gaa cct cca gaa aac tat gac aaa gaa gaa ttt tct cgc att caa    192
Met Glu Pro Pro Glu Asn Tyr Asp Lys Glu Glu Phe Ser Arg Ile Gln
    50                  55                  60 aaa gcc gct gaa aag att aaa tca gat agc gaa gta ctc gtg gtt att    240
Lys Ala Ala Glu Lys Ile Lys Ser Asp Ser Glu Val Leu Val Val Ile
65                  70                  75                  80
```

```
ggt att ggt ggt tcg tac ctt ggt gca aaa gca gca att gac ttt ttg      288
Gly Ile Gly Gly Ser Tyr Leu Gly Ala Lys Ala Ala Ile Asp Phe Leu
             85                  90                  95 aat aat cat ttt gct aat ttg caa acc gca gaa gaa cgt aaa gcg cct      336
Asn Asn His Phe Ala Asn Leu Gln Thr Ala Glu Glu Arg Lys Ala Pro
        100                 105                 110 cag att ctt tat gct gga aat tct att tca tct act tac ctt gcc gat      384
Gln Ile Leu Tyr Ala Gly Asn Ser Ile Ser Ser Thr Tyr Leu Ala Asp
            115                 120                 125 tta gtt gaa tac gtc caa gat aaa gaa ttc tca gta aat gtc att tca      432
Leu Val Glu Tyr Val Gln Asp Lys Glu Phe Ser Val Asn Val Ile Ser
        130                 135                 140 aaa tca ggt aca aca act gaa cca gcg att gct ttc cgt gta ttt aaa      480
Lys Ser Gly Thr Thr Thr Glu Pro Ala Ile Ala Phe Arg Val Phe Lys
145                 150                 155                 160 gaa ctt cta gtt aaa aag tac cgg tca aga aga agc                      516
Glu Leu Leu Val Lys Lys Tyr Arg Ser Arg Arg Ser
                165                 170
```

<210> SEQ ID NO 6
<211> LENGTH: 172
<212> TYPE: PRT
<213> ORGANISM: Streptococcus agalactiae

<400> SEQUENCE: 6

```
Met Thr His Ile Thr Phe Asp Leu Phe Lys Val Leu Gly Gln Phe Val
1               5                   10                  15

Gly Glu His Glu Leu Asp Tyr Leu Pro Pro Gln Val Ser Ala Ala Asp
            20                  25                  30

Ala Phe Leu Arg Gln Gly Thr Gly Pro Gly Ser Asp Phe Leu Gly Trp
        35                  40                  45

Met Glu Pro Pro Glu Asn Tyr Asp Lys Glu Phe Ser Arg Ile Gln
    50                  55                  60

Lys Ala Ala Glu Lys Ile Lys Ser Asp Ser Glu Val Leu Val Val Ile
65                  70                  75                  80

Gly Ile Gly Gly Ser Tyr Leu Gly Ala Lys Ala Ala Ile Asp Phe Leu
                85                  90                  95

Asn Asn His Phe Ala Asn Leu Gln Thr Ala Glu Glu Arg Lys Ala Pro
            100                 105                 110

Gln Ile Leu Tyr Ala Gly Asn Ser Ile Ser Ser Thr Tyr Leu Ala Asp
        115                 120                 125

Leu Val Glu Tyr Val Gln Asp Lys Glu Phe Ser Val Asn Val Ile Ser
    130                 135                 140

Lys Ser Gly Thr Thr Thr Glu Pro Ala Ile Ala Phe Arg Val Phe Lys
145                 150                 155                 160

Glu Leu Leu Val Lys Lys Tyr Arg Ser Arg Arg Ser
                165                 170
```

<210> SEQ ID NO 7
<211> LENGTH: 318
<212> TYPE: DNA
<213> ORGANISM: Streptococcus agalactiae
<220> FEATURE:
<221> NAME/KEY: CDS
<222> LOCATION: (1)..(318)
<223> OTHER INFORMATION:

<400> SEQUENCE: 7

```
att aac cga aga ttt aga tgg tct tgg tta tct tca aga aaa gat gta       48
```

```
                Ile Asn Arg Arg Phe Arg Trp Ser Trp Leu Ser Ser Arg Lys Asp Val
                1               5                   10                  15 gat ttt gtt aat aaa aaa gca aca gat ggt gtg ctt ctt gct cat aca                 96
Asp Phe Val Asn Lys Lys Ala Thr Asp Gly Val Leu Leu Ala His Thr
                20                  25                  30 gat ggt ggg gtt cca aat atg ttt gta acg ctt cct aca caa gac gct                144
Asp Gly Gly Val Pro Asn Met Phe Val Thr Leu Pro Thr Gln Asp Ala
            35                  40                  45 tac act ctt ggt tac act att tac ttc ttt gag tta gca att ggc ctt                192
Tyr Thr Leu Gly Tyr Thr Ile Tyr Phe Phe Glu Leu Ala Ile Gly Leu
    50                  55                  60 tca ggt tat ctt aac tca gta aat cca ttt gat caa ccg ggg gta gaa                240
Ser Gly Tyr Leu Asn Ser Val Asn Pro Phe Asp Gln Pro Gly Val Glu
65                  70                  75                  80 gca tat aaa cgt aat atg ttc gca ttt ggt aaa cct gga ttc gaa gag                288
Ala Tyr Lys Arg Asn Met Phe Ala Phe Gly Lys Pro Gly Phe Glu Glu
                85                  90                  95 ctt agc gct gaa ttg aat gca cgt ctt taa                                        318
Leu Ser Ala Glu Leu Asn Ala Arg Leu
                100                 105

<210> SEQ ID NO 8
<211> LENGTH: 105
<212> TYPE: PRT
<213> ORGANISM: Streptococcus agalactiae

<400> SEQUENCE: 8

Ile Asn Arg Arg Phe Arg Trp Ser Trp Leu Ser Ser Arg Lys Asp Val
1               5                   10                  15

Asp Phe Val Asn Lys Lys Ala Thr Asp Gly Val Leu Leu Ala His Thr
                20                  25                  30

Asp Gly Gly Val Pro Asn Met Phe Val Thr Leu Pro Thr Gln Asp Ala
            35                  40                  45

Tyr Thr Leu Gly Tyr Thr Ile Tyr Phe Phe Glu Leu Ala Ile Gly Leu
    50                  55                  60

Ser Gly Tyr Leu Asn Ser Val Asn Pro Phe Asp Gln Pro Gly Val Glu
65                  70                  75                  80

Ala Tyr Lys Arg Asn Met Phe Ala Phe Gly Lys Pro Gly Phe Glu Glu
                85                  90                  95

Leu Ser Ala Glu Leu Asn Ala Arg Leu
                100                 105

<210> SEQ ID NO 9
<211> LENGTH: 804
<212> TYPE: DNA
<213> ORGANISM: Streptococcus agalactiae
<220> FEATURE:
<221> NAME/KEY: CDS
<222> LOCATION: (1)..(804)
<223> OTHER INFORMATION:

<400> SEQUENCE: 9 atg aca tta tta gaa aaa att aat gag act aga gac ttt ttg caa gca                 48
Met Thr Leu Leu Glu Lys Ile Asn Glu Thr Arg Asp Phe Leu Gln Ala
1               5                   10                  15 aaa ggc gtc aca gca cca gaa ttt ggy ctt att tta ggc tct ggt tta                 96
Lys Gly Val Thr Ala Pro Glu Phe Gly Leu Ile Leu Gly Ser Gly Leu
                20                  25                  30 gga gaa ttg gct gaa gaa atc gaa aat cct att gtt gtg gat tat gca                144
Gly Glu Leu Ala Glu Glu Ile Glu Asn Pro Ile Val Val Asp Tyr Ala
            35                  40                  45
```

```
gac atc ccm aat tgg gga cag tca aca gta gtt ggt cat gct gga aaa       192
Asp Ile Pro Asn Trp Gly Gln Ser Thr Val Val Gly His Ala Gly Lys
         50                  55                  60 ttt agt gta tgg gat tta tca ggc cgt aag gta tta gcg ctt caa ggt       240
Phe Ser Val Trp Asp Leu Ser Gly Arg Lys Val Leu Ala Leu Gln Gly
 65                  70                  75                  80 cgt ttt cat ttt tay gaa ggw aat aca atg gaa gtc gtt act ttc cca       288
Arg Phe His Phe Tyr Glu Gly Asn Thr Met Glu Val Val Thr Phe Pro
                     85                  90                  95 gta cgt atc atg aga gca ttg gct tgc cac agt gtg ctt gtg act aat       336
Val Arg Ile Met Arg Ala Leu Ala Cys His Ser Val Leu Val Thr Asn
                 100                 105                 110 gca gcg ggt ggg att gga tac gga cca gga act tta atg ctg atc aaa       384
Ala Ala Gly Gly Ile Gly Tyr Gly Pro Gly Thr Leu Met Leu Ile Lys
             115                 120                 125 gac cac atc aat atg att ggg act aac cct ctc ata ggt gag aac ctt       432
Asp His Ile Asn Met Ile Gly Thr Asn Pro Leu Ile Gly Glu Asn Leu
         130                 135                 140 gaa gaa ttt gga cca cgt ttc cca gac atg tcg gat gct tay aca gca       480
Glu Glu Phe Gly Pro Arg Phe Pro Asp Met Ser Asp Ala Tyr Thr Ala
145                 150                 155                 160 aca tat cga caa aaa gct cac caa att gct gaa aac gat atc aaa ctc       528
Thr Tyr Arg Gln Lys Ala His Gln Ile Ala Glu Asn Asp Ile Lys Leu
                 165                 170                 175 gaa gaa ggt gtg tac ttg ggt gta tca gga ccc act tat gaa aca cct       576
Glu Glu Gly Val Tyr Leu Gly Val Ser Gly Pro Thr Tyr Glu Thr Pro
             180                 185                 190 gca gaa att cgt gca ttc caa aca atg ggc gca caa gcg gta ggt atg       624
Ala Glu Ile Arg Ala Phe Gln Thr Met Gly Ala Gln Ala Val Gly Met
         195                 200                 205 tcc acg gtt cca gag gtg atc gtt gca gct cac tca ggg ctt aaa gtg       672
Ser Thr Val Pro Glu Val Ile Val Ala Ala His Ser Gly Leu Lys Val
     210                 215                 220 tta gga att tca gca att act aac ctt gcc gct ggc ttc caa tca gag       720
Leu Gly Ile Ser Ala Ile Thr Asn Leu Ala Ala Gly Phe Gln Ser Glu
225                 230                 235                 240 ctc aat cat gag gag gtc gtt gaa gtt act cag cgt att aaa gaa gat       768
Leu Asn His Glu Glu Val Val Glu Val Thr Gln Arg Ile Lys Glu Asp
                 245                 250                 255 ttc aag gga tta ggt aaa tca tta gtt gct gaa ctc                       804
Phe Lys Gly Leu Gly Lys Ser Leu Val Ala Glu Leu
             260                 265

<210> SEQ ID NO 10
<211> LENGTH: 268
<212> TYPE: PRT
<213> ORGANISM: Streptococcus agalactiae

<400> SEQUENCE: 10

Met Thr Leu Leu Glu Lys Ile Asn Glu Thr Arg Asp Phe Leu Gln Ala
 1               5                  10                  15

Lys Gly Val Thr Ala Pro Glu Phe Gly Leu Ile Leu Gly Ser Gly Leu
             20                  25                  30

Gly Glu Leu Ala Glu Glu Ile Glu Asn Pro Ile Val Val Asp Tyr Ala
         35                  40                  45

Asp Ile Pro Asn Trp Gly Gln Ser Thr Val Val Gly His Ala Gly Lys
     50                  55                  60

Phe Ser Val Trp Asp Leu Ser Gly Arg Lys Val Leu Ala Leu Gln Gly
 65                  70                  75                  80
```

```
Arg Phe His Phe Tyr Glu Gly Asn Thr Met Glu Val Val Thr Phe Pro
                85                  90                  95

Val Arg Ile Met Arg Ala Leu Ala Cys His Ser Val Leu Val Thr Asn
            100                 105                 110

Ala Ala Gly Gly Ile Gly Tyr Gly Pro Gly Thr Leu Met Leu Ile Lys
        115                 120                 125

Asp His Ile Asn Met Ile Gly Thr Asn Pro Leu Ile Gly Glu Asn Leu
    130                 135                 140

Glu Glu Phe Gly Pro Arg Phe Pro Asp Met Ser Asp Ala Tyr Thr Ala
145                 150                 155                 160

Thr Tyr Arg Gln Lys Ala His Gln Ile Ala Glu Asn Asp Ile Lys Leu
                165                 170                 175

Glu Glu Gly Val Tyr Leu Gly Val Ser Gly Pro Thr Tyr Glu Thr Pro
            180                 185                 190

Ala Glu Ile Arg Ala Phe Gln Thr Met Gly Ala Gln Ala Val Gly Met
        195                 200                 205

Ser Thr Val Pro Glu Val Ile Val Ala Ala His Ser Gly Leu Lys Val
    210                 215                 220

Leu Gly Ile Ser Ala Ile Thr Asn Leu Ala Ala Gly Phe Gln Ser Glu
225                 230                 235                 240

Leu Asn His Glu Glu Val Val Glu Val Thr Gln Arg Ile Lys Glu Asp
                245                 250                 255

Phe Lys Gly Leu Gly Lys Ser Leu Val Ala Glu Leu
                260                 265

<210> SEQ ID NO 11
<211> LENGTH: 1428
<212> TYPE: DNA
<213> ORGANISM: Streptococcus agalactiae
<220> FEATURE:
<221> NAME/KEY: CDS
<222> LOCATION: (1)..(1428)
<223> OTHER INFORMATION:

<400> SEQUENCE: 11 ttg aca aaa gaa tat caa aat tat gtc aat ggc gaa tgg aaa tca tct      48
Leu Thr Lys Glu Tyr Gln Asn Tyr Val Asn Gly Glu Trp Lys Ser Ser
1               5                   10                  15 gtt aat cag att gag att ttg tca cca att gat gat tct tca ttg gga      96
Val Asn Gln Ile Glu Ile Leu Ser Pro Ile Asp Asp Ser Ser Leu Gly
            20                  25                  30 ttc gtg cca gcg atg act cga gaa gaa gtt gat cat gct atg aaa gcg     144
Phe Val Pro Ala Met Thr Arg Glu Glu Val Asp His Ala Met Lys Ala
        35                  40                  45 ggt cgt gag gct tta cca gct tgg gct gct tta aca gta tat gaa cgt     192
Gly Arg Glu Ala Leu Pro Ala Trp Ala Ala Leu Thr Val Tyr Glu Arg
    50                  55                  60 gca caa tac ctt cat aaa gcc gca gac att att gaa cgt gat aaa gaa     240
Ala Gln Tyr Leu His Lys Ala Ala Asp Ile Ile Glu Arg Asp Lys Glu
65                  70                  75                  80 gaa att gct act gtt tta gca aaa gaa att tct aaa gct tac aat gct     288
Glu Ile Ala Thr Val Leu Ala Lys Glu Ile Ser Lys Ala Tyr Asn Ala
                85                  90                  95 tca gta act gag gtt gta agg aca gct gat ctt att cgt tat gca gca     336
Ser Val Thr Glu Val Val Arg Thr Ala Asp Leu Ile Arg Tyr Ala Ala
            100                 105                 110 gaa gaa gga att cgt tta tca act tca gct gac gaa ggt gga aaa atg     384
Glu Glu Gly Ile Arg Leu Ser Thr Ser Ala Asp Glu Gly Gly Lys Met
        115                 120                 125
```

```
                  115                 120                 125
gat gct tca aca ggt cat aag ttg gct gtt att cgt cgt caa cca gta    432
Asp Ala Ser Thr Gly His Lys Leu Ala Val Ile Arg Arg Gln Pro Val
    130                 135                 140 ggt atc gtt tta gca atc gca cct tat aat tac cct gtt aac ctc tca    480
Gly Ile Val Leu Ala Ile Ala Pro Tyr Asn Tyr Pro Val Asn Leu Ser
145                 150                 155                 160 gga tca aaa att gcg cca gct cta att ggt gga aac gtt gtg atg ttt    528
Gly Ser Lys Ile Ala Pro Ala Leu Ile Gly Gly Asn Val Val Met Phe
                165                 170                 175 aaa cca cca aca caa ggt tca gtc tca gga ctt gtt tta gca aaa gct    576
Lys Pro Pro Thr Gln Gly Ser Val Ser Gly Leu Val Leu Ala Lys Ala
            180                 185                 190 ttt gca gaa gca ggt ctt cca gca ggt gtc ttt aat act att aca gga    624
Phe Ala Glu Ala Gly Leu Pro Ala Gly Val Phe Asn Thr Ile Thr Gly
        195                 200                 205 cgc ggt tct gag att gga gat tac att gtt gag cat gaa gaa gtt aat    672
Arg Gly Ser Glu Ile Gly Asp Tyr Ile Val Glu His Glu Glu Val Asn
    210                 215                 220 ttt att aac ttt aca gga tca acg cca gtt gga caa cgt att ggt aag    720
Phe Ile Asn Phe Thr Gly Ser Thr Pro Val Gly Gln Arg Ile Gly Lys
225                 230                 235                 240 ttg gca gga atg cgt cca att atg ctt gag ttg ggc ggt aag gat gca    768
Leu Ala Gly Met Arg Pro Ile Met Leu Glu Leu Gly Gly Lys Asp Ala
                245                 250                 255 ggt atc gtc tta gct gat gct gac ctt gat aac gct gct aaa caa atc    816
Gly Ile Val Leu Ala Asp Ala Asp Leu Asp Asn Ala Ala Lys Gln Ile
            260                 265                 270 gtt gca ggt gct tat gat tac tct gga caa cgc tgt acg gca att aag    864
Val Ala Gly Ala Tyr Asp Tyr Ser Gly Gln Arg Cys Thr Ala Ile Lys
        275                 280                 285 cgt gtg ctt gtc gtt gaa gaa gtt gcw gat gaa ttg gca gaa aaa ata    912
Arg Val Leu Val Val Glu Glu Val Ala Asp Glu Leu Ala Glu Lys Ile
    290                 295                 300 tct gaa aat gta gca aaa tta tca gta ggt gat cca ttt gat aat gca    960
Ser Glu Asn Val Ala Lys Leu Ser Val Gly Asp Pro Phe Asp Asn Ala
305                 310                 315                 320 acg gtg aca ccg gtt att gat gat aat tca gct gac ttt att gaa agc    1008
Thr Val Thr Pro Val Ile Asp Asp Asn Ser Ala Asp Phe Ile Glu Ser
                325                 330                 335 tta gta gta gat gca cgt caa aaa ggt gcg aaa gaa ttg aat gaa ttt    1056
Leu Val Val Asp Ala Arg Gln Lys Gly Ala Lys Glu Leu Asn Glu Phe
            340                 345                 350 aaa cgt gat ggt cgt cta tta act cca gga ttg ttt gat cat gtt act    1104
Lys Arg Asp Gly Arg Leu Leu Thr Pro Gly Leu Phe Asp His Val Thr
        355                 360                 365 tta gat atg aaa cta gct tgg gaa gag cct ttt gga cca att ctc cca    1152
Leu Asp Met Lys Leu Ala Trp Glu Glu Pro Phe Gly Pro Ile Leu Pro
    370                 375                 380 att att cgt gtc aag gat gca gaa gaa gct gtt gct att gcc aac aaa    1200
Ile Ile Arg Val Lys Asp Ala Glu Glu Ala Val Ala Ile Ala Asn Lys
385                 390                 395                 400 tct gat ttt gga tta caa tca tca gtc ttt aca cgt gat ttc caa aaa    1248
Ser Asp Phe Gly Leu Gln Ser Ser Val Phe Thr Arg Asp Phe Gln Lys
                405                 410                 415 gca ttt gat ata gca aat aaa ctt gaa gtt ggt aca gtt cac att aac    1296
Ala Phe Asp Ile Ala Asn Lys Leu Glu Val Gly Thr Val His Ile Asn
            420                 425                 430 aat aag act gga cgt ggt ccw gat aat ttc cca ttc tta gga ctc aaa    1344
```

-continued

```
Asn Lys Thr Gly Arg Gly Pro Asp Asn Phe Pro Phe Leu Gly Leu Lys
        435                 440                 445 gga tct ggt gca ggt gtt caa ggt atc aga tat tca att gaa gca atg    1392
Gly Ser Gly Ala Gly Val Gln Gly Ile Arg Tyr Ser Ile Glu Ala Met
450                 455                 460 aca aat gta aaa tcg att gtt ctc gat atg aaa tag                    1428
Thr Asn Val Lys Ser Ile Val Leu Asp Met Lys
465                 470                 475
```

<210> SEQ ID NO 12
<211> LENGTH: 475
<212> TYPE: PRT
<213> ORGANISM: Streptococcus agalactiae

<400> SEQUENCE: 12

```
Leu Thr Lys Glu Tyr Gln Asn Tyr Val Asn Gly Glu Trp Lys Ser Ser
1               5                  10                  15

Val Asn Gln Ile Glu Ile Leu Ser Pro Ile Asp Asp Ser Ser Leu Gly
            20                  25                  30

Phe Val Pro Ala Met Thr Arg Glu Glu Val Asp His Ala Met Lys Ala
        35                  40                  45

Gly Arg Glu Ala Leu Pro Ala Trp Ala Ala Leu Thr Val Tyr Glu Arg
    50                  55                  60

Ala Gln Tyr Leu His Lys Ala Ala Asp Ile Ile Glu Arg Asp Lys Glu
65                  70                  75                  80

Glu Ile Ala Thr Val Leu Ala Lys Glu Ile Ser Lys Ala Tyr Asn Ala
                85                  90                  95

Ser Val Thr Glu Val Val Arg Thr Ala Asp Leu Ile Arg Tyr Ala Ala
            100                 105                 110

Glu Glu Gly Ile Arg Leu Ser Thr Ser Ala Asp Glu Gly Gly Lys Met
        115                 120                 125

Asp Ala Ser Thr Gly His Lys Leu Ala Val Ile Arg Arg Gln Pro Val
130                 135                 140

Gly Ile Val Leu Ala Ile Ala Pro Tyr Asn Tyr Pro Val Asn Leu Ser
145                 150                 155                 160

Gly Ser Lys Ile Ala Pro Ala Leu Ile Gly Gly Asn Val Val Met Phe
                165                 170                 175

Lys Pro Pro Thr Gln Gly Ser Val Ser Gly Leu Val Leu Ala Lys Ala
            180                 185                 190

Phe Ala Glu Ala Gly Leu Pro Ala Gly Val Phe Asn Thr Ile Thr Gly
        195                 200                 205

Arg Gly Ser Glu Ile Gly Asp Tyr Ile Val Glu His Glu Glu Val Asn
    210                 215                 220

Phe Ile Asn Phe Thr Gly Ser Thr Pro Val Gly Gln Arg Ile Gly Lys
225                 230                 235                 240

Leu Ala Gly Met Arg Pro Ile Met Leu Glu Leu Gly Gly Lys Asp Ala
                245                 250                 255

Gly Ile Val Leu Ala Asp Ala Asp Leu Asp Asn Ala Ala Lys Gln Ile
            260                 265                 270

Val Ala Gly Ala Tyr Asp Tyr Ser Gly Gln Arg Cys Thr Ala Ile Lys
        275                 280                 285

Arg Val Leu Val Val Glu Glu Val Ala Asp Glu Leu Ala Glu Lys Ile
    290                 295                 300

Ser Glu Asn Val Ala Lys Leu Ser Val Gly Asp Pro Phe Asp Asn Ala
305                 310                 315                 320
```

-continued

```
Thr Val Thr Pro Val Ile Asp Asp Asn Ser Ala Asp Phe Ile Glu Ser
            325                 330                 335

Leu Val Val Asp Ala Arg Gln Lys Gly Ala Lys Glu Leu Asn Glu Phe
            340                 345                 350

Lys Arg Asp Gly Arg Leu Leu Thr Pro Gly Leu Phe Asp His Val Thr
            355                 360                 365

Leu Asp Met Lys Leu Ala Trp Glu Glu Pro Phe Gly Pro Ile Leu Pro
            370                 375                 380

Ile Ile Arg Val Lys Asp Ala Glu Glu Ala Val Ala Ile Ala Asn Lys
385                 390                 395                 400

Ser Asp Phe Gly Leu Gln Ser Ser Val Phe Thr Arg Asp Phe Gln Lys
            405                 410                 415

Ala Phe Asp Ile Ala Asn Lys Leu Glu Val Gly Thr Val His Ile Asn
            420                 425                 430

Asn Lys Thr Gly Arg Gly Pro Asp Asn Phe Pro Phe Leu Gly Leu Lys
            435                 440                 445

Gly Ser Gly Ala Gly Val Gln Gly Ile Arg Tyr Ser Ile Glu Ala Met
    450                 455                 460

Thr Asn Val Lys Ser Ile Val Leu Asp Met Lys
465                 470                 475
```

NADP-DEPENDENT GLYCERALDEHYDE-3-PHOSPHATE DEHYDROGENASE FOR THERAPEUTIC USE

CROSS-REFERENCE TO RELATED APPLICATION

This application is the National Stage of International Application No. PCT/GB99/04376, filed Dec. 22, 1999.

FIELD OF THE INVENTION

This invention relates to the identification of outer surface proteins, their genes, and their use. More particularly, it relates to their use in therapy, for immunisation and in screening for drugs.

BACKGROUND TO THE INVENTION

Group B *Streptococcus* (GBS), also known as *Streptococcus agalactiae*, is the causative agent of various conditions. In particular, GBS causes:

Early Onset Neonatal Infection.

This infection usually begins in utero and causes severe septicaemia and pneumonia in infants, which is lethal if untreated and even with treatment is associated with a 10–20% mortality rate. Late onset neonatal infection.

This infection occurs in the period shortly after birth until about 3 months of age. It causes a septicaemia, which is complicated by meningitis in 90% of cases. Other focal infections also occur including osteomyelitis, septic arthritis, abscesses and endopthalmitis.

Adult Infections.

These appear to be increasingly common and occur most frequently in women who have just delivered a baby, the elderly and the immunocompromised. They are characterised by septicaemia and focal infections including osteomyelitis, septic arthritis, abscesses and endopthalmitis.

Urinary Tract Infections.

GBS is a cause of urinary tract infections and in pregnancy accounts for about 10% of all infections.

Veterinary Infections.

GBS causes chronic mastitis in cows. This, in turn, leads to reduced milk production and is therefore of considerable economic importance.

GBS infections can be treated with antibiotics. However, immunisation is preferable. It is therefore desirable to develop an immunogen that could be used in a therapeutically-effective vaccine.

SUMMARY OF THE INVENTION

The present invention is based on the identification of a series of genes in GBS, and also related organisms, the products of which may be associated with the outer surface of the organism and may therefore be useful as targets for immunotherapy.

According to one aspect of the invention, a peptide is encoded by an operon including any of the genes identified herein as MS4, MS10, MS11, MS14 and MS16, obtainable from Group B *Streptococcus*, or a homologue or functional fragment thereof. Such a peptide is suitable for therapeutic use, e.g. when isolated.

The term "functional fragments" is used herein to define a part of the gene or peptide which retains the activity of the whole gene or peptide. For example, a functional fragment of the peptide may be used as an antigenic determinant, useful in a vaccine or in the production of antibodies.

A gene fragment may be used to encode the active peptide. Alternatively, the gene fragment may have utility in gene therapy, targetting the wild-type gene in vivo to exert a therapeutic effect.

A peptide according to the present invention may comprise any of the amino acid sequences identified herein as SEQ ID NOS. 2, 4, 6, 8, 10 and 12, or a functional fragment thereof.

Because of the extracellular or cell surface location, the peptides of the present invention may be suitable candidates for the production of therapeutically-effective vaccines against GBS. The term "therapeutically-effective" is intended to include the prophylactic effect of vaccines. For example, a vaccine may comprise a peptide according to the invention, or the means for its expression, for the treatment of infection.

This vaccine may be administered to females either prior to or during pregnancy to protect mother and neonate against infection by GBS.

According to another aspect of the invention, the peptides or genes may be used for screening potential antimicrobial drugs or for the detection of virulence.

A further aspect of this invention is the use of any of the products identified herein, for the treatment or prevention of a condition associated with infection by a Group B *Streptococcal* strain.

Although the protein has been described for use in the treatment of patients, veterinary uses of the products of the invention are also considered to be within the scope of the present invention. In particular, the peptides or the vaccines may be used in the treatment of chronic mastitis, especially in cows.

DESCRIPTION OF THE INVENTION

The present invention is described with reference to Group B *Streptococcal* strain M732. However, all the GBS strains and many other bacterial strains are likely to include related peptides or proteins having amino acid sequence homology with the peptide of M732. Organisms likely to contain the peptides include, but are not limited to, *S. pneumoniae, S. pyogenes, S. suis, S. milleri*, Group C and Group G *Streptococci* and *Enterococci*. Vaccines to each of these may be developed in the same way as described for GBS.

Preferably, the peptides that may be useful for the production of vaccines have greater than 40% sequence similarity with the peptides identified herein. More preferably, the peptides have greater than 60% sequence similarity. Most preferably, the peptides have greater than 80% sequence similarity, e.g. 95% similarity.

Having characterised a gene according to the invention, it is possible to use the gene sequence to establish homologies in other microorganisms. In this way it is possible to determine whether other microorganisms have similar outer surface products. Sequence homologies may be established by searching in existing databases, e.g. EMBL or Genbank.

Peptides or proteins according to the invention may be purified and isolated by methods known in the art. In particular, having identified the gene sequence, it will be possible to use recombinant techniques to express the genes in a suitable host. Active fragments and homologues can be identified and may be useful in therapy. For example, the peptides or their active fragments may be used as antigenic determinants in a vaccine, to elicit an immune response. They may also be used in the preparation of antibodies, for passive immunisation, or diagnostic applications. Suitable antibodies include monoclonal antibodies, or fragments thereof, including single chain fv fragments. Methods for the preparation of antibodies will be apparent to those skilled in the art.

The preparation of vaccines based on attenuated microorganisms is known to those skilled in the art. Vaccine compositions can be formulated with suitable carriers or adjuvants, e.g. alum, as necessary or desired, and used in therapy, to provide effective immunisation against Group B *Streptococci* or other related microorganisms. The preparation of vaccine formulations will be apparent to the skilled person.

More generally, and as is well known to those skilled in the art, a suitable amount of an active component of the invention can be selected, for therapeutic use, as can suitable carriers or excipients, and routes of administration. These factors will be chosen or determined according to known criteria such as the nature/severity of the condition to be treated, the type or health of the subject etc.

The products of the present invention were identified as follows:

Todd-Hewitt broth was inoculated with GBS and allowed to grow overnight at 37° C. The cells were harvested by centrifugation and washed with Phosphate Buffered Saline (PBS). The cells were resuspended in an osmotic buffer (20% (w/v) Sucrose, 20 mM Tris-HCl pH 7.0, 10 mM $MgCl_2$) containing protease inhibitors (1 mM PMSF, 10 μM Iodoeacetic Acid, 10 mM 1,10-Phenanthroline, 1 μM Pepstatin A) and Mutanolysin at a final concentration of 4 Units per microlitre. This was incubated (shaking) at 37° C. for 2 hours.

Cells and debris were removed first by high speed centrifugation, then ultra-centrifugation for 1 hour. The resultant supernatant containing cell wall proteins was concentrated under pressure using an ultrafiltration device (10,000 molecular weight cut-off).

The sample was dialysed against ultra high quality water and lyophilised. After resuspension in loading buffer, the proteins were separated by preparative 2-Dimensional-Gel Electrophoresis. Following electrophoresis an individual spot was chosen for study. The spot was subjected to in-gel tryptic digestion. The resulting peptides were extracted from the gel and purified using microbore RP-HPLC. Fractions were collected every 45 seconds and a portion of these consistent with the regions of UV absorbance were analysed by Delayed Extraction-Matrix Assisted Laser Desorption-Time of Flight Mass Spectrometry (DE-MALDI-TOF-MS). Peptides not observed in a blank preparation were then subjected to sequencing using Nanospray-MS/MS Using this peptide sequence information, degenerate oligonucleotides were designed to be used in a polymerase chain reaction (PCR) to amplify the DNA segment lying between the peptide sequences identified.

PCR amplification resulted in the production of several polynucleotide fragments, each of which was cloned into the pCR 2.1-TOPO vector (Invitrogen BV, Netherlands) according to manufacturers protocol.

The DNA fragment in each plasmid was identified by sequencing and then used to obtain the full-length gene sequence, as follows:

Using the identified DNA fragment, oligonucleotide primers were designed for genomic DNA sequencing. These primers were designed so as to sequence in an 'outward' direction from the obtained sequence. Once read, the sequence obtained was checked to see if the 5' and 3' termini of the gene had been reached. The presence of these features was identified by checking against homologous sequences, and for the 5' end the presence of an AUG start codon (or accepted alternative) preceded by a Shine-Dalgarno consensus sequence, and for the 3' end, the presence of a translation termination (Stop) codon.

Upon identification of the full-length gene, primers were designed for amplification of full-length product from GBS genomic DNA. Primers used included restriction enzyme recognition sites (NcoI at the 5'end and EcoO109I at the 3' end) to allow subsequent cloning of the product into the Lactococcal expression system used.

PCR was carried out using the primers, and the products cloned into a pCR 2.1 cloning vector (In Vitrogen). Following confirmation of the presence of the cloned fragment, the DNA was excised using the restriction enzymes NcoI and EcoO109I.

The vector into which this fragment was inserted was a modified version of pNZ8048 (Kuipers, O. P. et al. (1998) J. Biotech 64: 15–21). This vector, harbouring a lactococcal origin of replication, a chloramphenicol resistance marker, an inducible nisin promoter and a multicloning site was altered by the replacement of the multicloning site with two 10×His tags, flanked on the 5-most end with an NcoI site, split in the middle with a multicloning site (including an EcoO109I site), and a Stop (termination) codon at the 3'end of the His tags.

The gene of interest was inserted so that a 10× His tag was in the 3' position relative to the coding region. Following transformation of the recombinant plasmid into *L.lactis* (strain NZ9000—Kuipers, O. P. et al. (1998) supra), a 400 ml liquid culture was set up and translation of the protein was induced by the addition of nisin to the culture. After a 2 hour incubation, the cells were harvested and lysed by bead beating. The resultant lysate was cleared by centrifugation, then passed over a metal affinity (Talon, Clonetech) column. The column was washed repeatedly before bound proteins were eluted with Imidazole.

To identify fractions containing the His-tagged recombinant protein, an aliquot from each fraction was analysed by SDS-PAGE, Western blotted and probed with anti-His antibodies.

The recombinant protein obtained was then used to immunise New Zealand white rabbits, with pre-immune sera being harvested prior to immunisation. Following a boost, the rabbits were sacrificed and sera collected. This sera was used in Western blots, ELISA and animal protection models.

Using the sera obtained from the animal studies, immunosorption studies were carried out.

Group B *Streptococcus* was grown in 20 ml Todd Hewitt broth (THB) for 8 hours, harvested and resuspended in 5 ml PBS. 50 μl aliquots of this were used to coat wells in a 96 well plate (Nunc Immuno-Sorb). This was left at 4° C. overnight to allow for absorbance of the bacteria onto the plate. Plates were washed twice with PBS, then blocked with 3% BSA in PBS for 1 hr at 37° C. Plates were again washed. Serial 10 fold dilutions of the sera were made in PBS and 501 of these dilutions were added to the wells of the plate, in duplicate. The plate was covered and incubated for 1 hr at 37° C. The plate was washed, then 50 μl anti-rabbit alkaline phosphatase conjugated secondary antibody at a concentration of 1:5000 was added to each well. Following incubation at 37° C. for an hour, the plate was washed again.

50 µl substrate (PNPP) was added to each well, and the reaction allowed to proceed for 30 min before the absorbance was read at 405 nm.

Animal protection studies were also carried out to test the effectiveness of protection on the immunised rabbits.

GBS M732 was grown up in THB until mid-log phase was reached—approximately 5 hours. Cells were counted in a counting chamber, and bacteria were diluted to give a concentration of $2\times10^7$ bacteria per ml in pre-immune or test sera. 50 µl of this was injected via the intraperitoneal route into 0–1 day old mice. The mice were observed for survival over 48 hours.

The following Examples illustrate the invention.

EXAMPLE 1

A first plasmid was termed MS4. The cloned DNA fragment was sequenced and the nucleotide and deduced amino acid sequence (SEQ ID NO. 1 and 2) was used to search protein databases.

Homologues to the GBS MS4 gene product can be identified in *Clostridium perfingens, Haemophilus influenzae, Neisseria flavescens* and *Thermatoga maritima*. In all cases the homologues are the genes for Ornithine Carbamoyltransferase (OCT). In eukaryotic systems this enzyme catalyses the second step in the Urea cycle, the conversion of ornithine to citrulline, a reaction requiring carbomyl phosphate. In prokaryotes, ODC is one of the three enzymes involved in Arginine Deaminase activity—a system which protects bacteria from acid damage. In particular, ODC is responsible for the conversion of citrulline to ornithine and carbamoyl phosphate (the opposite role to that in eukaryotes) (Casiano-Colon, A and Marquis, R. E. 1988. Appl. Environ. Microbiol. 54: 1318–1324, Cunin, R. et al. 1986. Microbiol. Rev. 50: 314–352).

Animal protection studies were, carried out as described above. The results are as follows:

| | | # pups surviving at time (hrs) | |
|---|---|---|---|
| Treatment | # pups | 24 | 48 |
| PBS | 15 | 6 | 0 |
| Pre-Immune | 41 | 18 | 1 |
| Test | 41 | 33 | 14 |

EXAMPLE 2

A second plasmid was termed MS11. The nucleotide and deduced amino acid sequence (SEQ ID NOS. 3 and 4) were used to search protein databases.

Homologues to the GBS MS11 gene product can be identified in *Lactobacillus delbrueckii, Thermotoga maritima, Clostridium acetobulylicum, Bacillus megaterium, Triticum aestivium* and *Synechocystis* PCC6803.

In all cases the homologues are the genes for the protein Phosphoglycerate Kinase (PGK). PGK is a major enzyme in the glycolytic pathway, being involved in the conversion of Glyceraldehyde-3-phosphate to Phosphoenolpyruvate. In particular, it is involved in the catalysis of the reaction between Glycerate-1,3-diphosphate and 3-Phospho-Glycerate, releasing a phosphate in the forward reaction.

EXAMPLE 3

A third plasmid was termed pMS16. The 5' and 3' cloned DNA fragments were sequenced and the nucleotide and deduced amino acid sequences for each are shown as SEQ ID NOS. 5 and 6 for the 5' fragment and SEQ ID NOS. 7 and 8 for the 3' fragment.

Homologues to the GBS MS16 gene product can be identified in *Bacillus stearothermophilus, Bacillus subtilis* and *Mycoplasma genitalium*.

In all cases the homologues are the genes for the protein Glucose-6-Phosphate Isomerase (GPI).

The enzyme Glucose-6-Phospate Isomerase catalyses the reaction between Glucose-6-phosphate and Fructose-6-Phosphate in both glycolysis (G6P to F6P) and gluconeogenesis (F6P to G6P). Mutations in the gpi gene have been shown to confer purine analogue sensitivity to organisms.

EXAMPLE 4

A fourth plasmid was termed pMS14. The cloned DNA fragment was sequenced and the nucleotide and deduced amino acid sequence (SEQ ID NOS. 9 and 10) was used to search protein databases.

Homologues to the GBS MS14 gene product can be identified in *Bacillus subtilis, Bacillus stearothermophilus, Mus musculus, Bos taurus* and *Zea mays*. In all cases the homologues are the genes for the protein Purine Nucleoside Phosphatase (PNP). The function of this enzyme is to cleave the nucleosides guanosine or inosine to their respective basis and sugar-1-phosphate molecules in the presence of orthophosphate.

EXAMPLE 5

A fifth plasmid was termed pMS10. The cloned DNA fragment was sequenced. The nucleotide and deduced amino acid sequence (SEQ ID NOS. 11 and 12) was used to search protein databases.

Homologues to the GBS MS10 gene product can be identified in *Streptococcus mutans, Nicotiana plumb, Pisum sativum* and *Zea mays*. In all cases the homologues are the genes for the protein Nonphosphorylating, NADP-Dependent Glyceraldehyde-3-Phosphate Dehydrogenase (NP-GAP-3-DH). NPGAP-3-DH has been reported as being an important means of generating NADPH for biosynthetic reactions in *S. mutans* (as opposed to NAD-specific GAP-3-DH which satisfies the requirements of the glycolytic pathway) (Boyd, D. A., Cvitkovitch, D. G. and Hamilton, I. R 1995 J. Bacteriol. 177: 2622–2727).

The invention claimed is:

1. A method for raising antibodies against Group B *Streptococcus*, comprising administering an isolated Group B *Streptococcal* non-phosphorylating NADP-dependent glyceraldehydo-3-phosphate dehydrogenase to a subject, wherein the non-phosphorylating NADP-dependent glyceraldehyde-3-phosphate dehydrogenase is administered in an amount effective to produce the antibodies.

2. The method, according to claim 1, wherein the non-phosphorylating NADP-dependent glyceraldehyde-3-phosphate dehydrogenase comprises SEQ ID NO:12.

3. The method according to claim 1, wherein the subject is female.

4. The method according to claim 1, wherein the subject is a pregnant female.

5. The method according to claim 2, wherein the subject is female.

6. The method according to claim 2, wherein the subject is a pregnant female.

* * * * *